(12) United States Patent
Namin et al.

(10) Patent No.: US 10,413,635 B2
(45) Date of Patent: Sep. 17, 2019

(54) UMBILICAL CORD TRANSPLANT PRODUCT

(71) Applicant: Vivex Biomedical, Inc., Marietta, GA (US)

(72) Inventors: Shabnam Namin, Miami, FL (US); Gaëtan Jean-Robert Delcroix, Miami, FL (US); Timothy Ganey, Tampa, FL (US); Lou Barnes, Miami, FL (US)

(73) Assignee: Vivex Biomedical, Inc., Atlanta, GA (US)

( * ) Notice: Subject to any disclaimer, the term of this patent is extended or adjusted under 35 U.S.C. 154(b) by 24 days.

(21) Appl. No.: 14/827,445

(22) Filed: Aug. 17, 2015

(65) Prior Publication Data
US 2017/0049928 A1  Feb. 23, 2017

(51) Int. Cl.
*A61L 27/36* (2006.01)
*A61F 2/00* (2006.01)
(Continued)

(52) U.S. Cl.
CPC ........ *A61L 27/3604* (2013.01); *A61F 2/0077* (2013.01); *A61F 2/04* (2013.01);
(Continued)

(58) Field of Classification Search
CPC .......... A61F 2002/041; A61F 2002/042; A61F 2002/043; A61F 2002/044;
(Continued)

(56) References Cited

U.S. PATENT DOCUMENTS 4,283,448 A * 8/1981 Bowman ................... A61F 2/06
428/34.9
4,778,467 A * 10/1988 Stensaas ............ A61B 17/1128
128/898

(Continued)

OTHER PUBLICATIONS

TWI. "What imperfections may laser drilled holes be prone to?". Downloaded from <http://www.twi-global.com/technical-knowledge/faqs/process-faqs/faq-what-imperfections-may-laser-drilled-holes-be-prone-to/> on Jun. 3, 2016.*

(Continued)

*Primary Examiner* — Suba Ganesan
(74) *Attorney, Agent, or Firm* — David L. King

(57) ABSTRACT

A transplant product derived from human umbilical cord has a collagenous tissue membrane derived from an umbilical cord, configured as a soft tissue barrier or wound covering or other internal or external wound healing attachment. The structural, chemical and biochemical properties are retained, the collagenous tissue membrane is cleaned removing the veins, arteries and Wharton's jelly without exposure to harsh chemicals. The collagenous tissue membrane is soaked in normal saline solution under mild agitation for a predetermined time to structurally increase tear resistance of the membrane. The collagenous tissue membrane is free of meconium. The collagenous tissue membrane has a general transparent or translucent appearance of a clear or slightly pink color. In one embodiment, the transplant product has one or more suture entry sites to facilitate suturing the product to tissue.

5 Claims, 8 Drawing Sheets

(51) Int. Cl.
*A61F 2/04* (2013.01)
*A61F 2/06* (2013.01)
*A61L 27/24* (2006.01)
*A61L 27/50* (2006.01)

(52) U.S. Cl.
CPC ............... *A61F 2/06* (2013.01); *A61L 27/24* (2013.01); *A61L 27/3695* (2013.01); *A61L 27/50* (2013.01); *A61L 2400/16* (2013.01); *A61L 2430/00* (2013.01); *A61L 2430/32* (2013.01)

(58) Field of Classification Search
CPC .......... A61F 2002/045; A61F 2002/046; A61F 2/04; A61F 2/06; A61F 2/07; A61F 2/92
See application file for complete search history.

(56) References Cited

U.S. PATENT DOCUMENTS

| | | | | |
|---|---|---|---|---|
| 6,254,627 | B1 * | 7/2001 | Freidberg | A61F 2/07 606/195 |
| 6,352,561 | B1 * | 3/2002 | Leopold | A61F 2/07 623/1.11 |
| 6,632,239 | B2 * | 10/2003 | Snyder | A61B 17/12 606/151 |
| 6,699,277 | B1 * | 3/2004 | Freidberg | A61F 2/07 623/1.13 |
| 8,087,413 | B2 * | 1/2012 | Saadat | A61B 17/00491 128/898 |
| 9,179,976 | B2 * | 11/2015 | Paulos | A61B 19/026 |
| 2007/0154515 | A1 * | 7/2007 | Johnson | A61L 31/005 424/423 |
| 2008/0131522 | A1 * | 6/2008 | Liu | A61K 35/44 424/583 |
| 2011/0054588 | A1 * | 3/2011 | Xu | A61L 27/3604 623/1.13 |
| 2012/0010728 | A1 * | 1/2012 | Sun | A61L 27/50 623/23.72 |
| 2012/0022630 | A1 * | 1/2012 | Wubbeling | A61F 2/95 623/1.11 |
| 2012/0141595 | A1 * | 6/2012 | Tseng | A61K 35/44 424/583 |

OTHER PUBLICATIONS

Trumpf. "Drilling". Downloaded from <http://www.trumpf-laser.com/en/solutions/applications/laser-cutting/drilling.html> on Jun. 3, 2016.*

Schulz et al. "Review on laser drilling 1. Fundamentals, modeling, and simulation". Journal of Laser Applications 25(1): Feb. 2013. 012006-1-012006-17.*

* cited by examiner

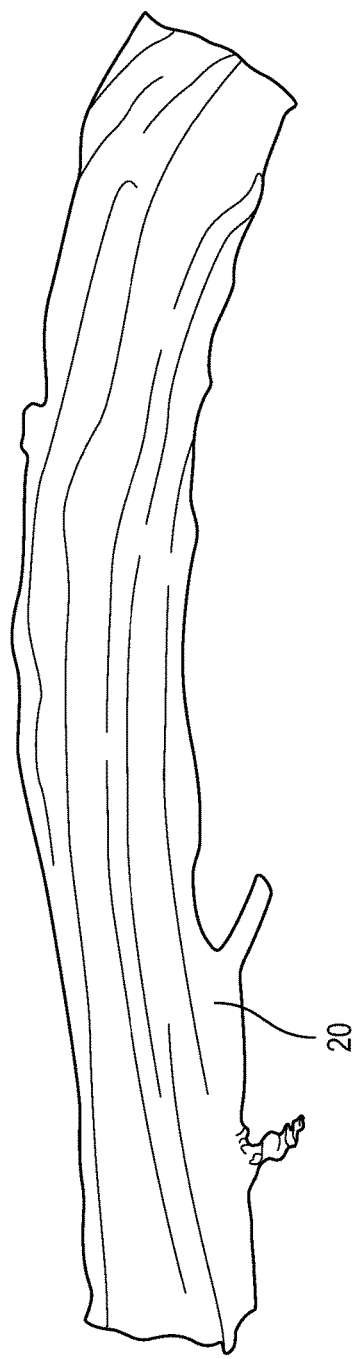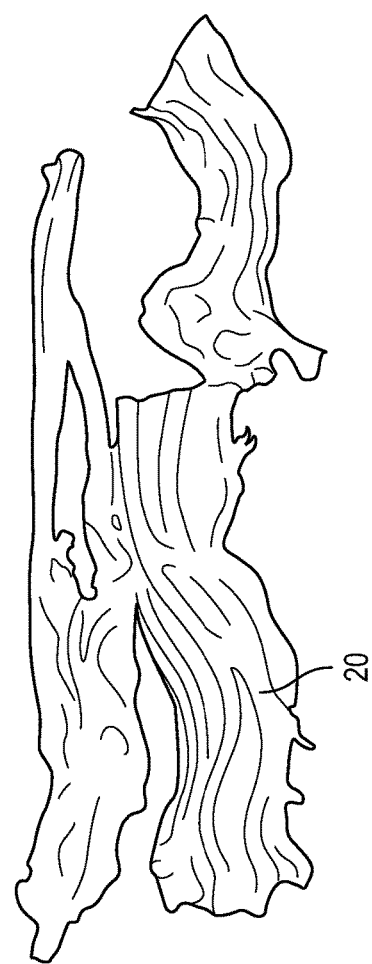
FIG. 3
FIG. 4

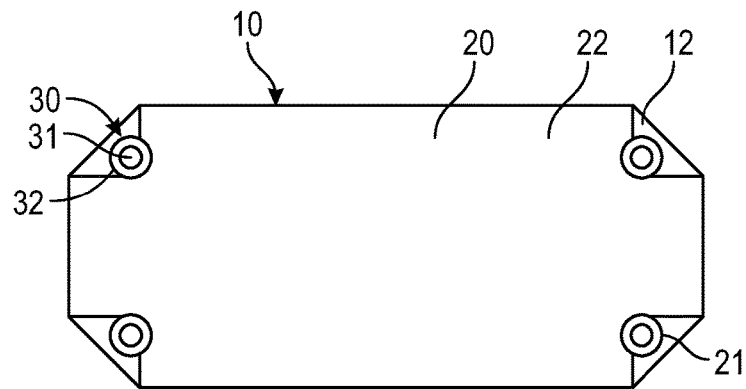
FIG. 12
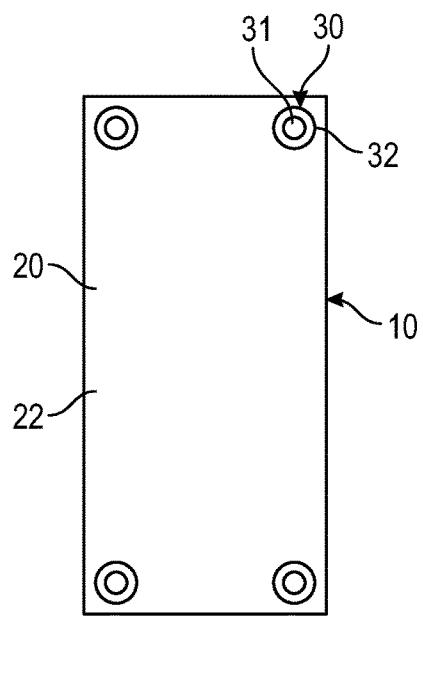 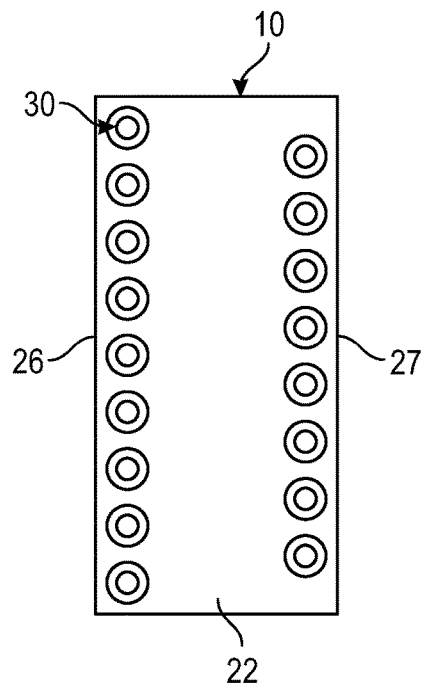
FIG. 13   FIG. 14

UMBILICAL CORD TRANSPLANT PRODUCT

TECHNICAL FIELD

This invention relates to a transplant product derived from human umbilical cord for use as a soft tissue barrier or wound covering or other internal or external healing attachment and the products method of manufacture.

BACKGROUND OF THE INVENTION

The use of placental tissue to harvest thin membranes of amnion or chorion is well known. The use of umbilical cords to harvest stem cells is also well documented. However, the use of the umbilical cord tissue as a source for wound covering has been avoided because of the very thick nature of the tubular umbilical cord tissue and the fact that it is such a thick material it is not considered readily absorbable during a normal soft tissue healing. All of these adverse preconceived notions in the medical community may be unwarranted, if not wrong, in many applications wherein the healing time is long or the thickness of the material can be an advantage. The inventors of the present invention have discovered a remarkable way to process the harvested umbilical cord that not only benefits from the otherwise perceived drawbacks, but in fact provides embodiments with heretofore unachievable attachment features that make suture tissue tears issue completely disappear while at the same time making the material easier to pass sutures compared to using thin amniotic membranes. All of this is accomplished without requiring an additional structural layers to prevent tissue suture tearouts.

SUMMARY OF THE INVENTION

A transplant product derived from human umbilical cord has a collagenous tissue membrane derived from an umbilical cord made essentially of thick collagenous tissue which is configured as a soft tissue barrier or wound covering or other internal or external wound healing attachment. The structural, chemical and biochemical properties are retained, the collagenous tissue membrane is cleaned removing the veins, arteries and Wharton's jelly without exposure to harsh chemicals. The collagenous tissue membrane is soaked in normal saline solution under mild agitation for a predetermined time to structurally increase tear resistance of the membrane. The collagenous tissue membrane is free of meconium. The collagenous tissue membrane has a general transparent or translucent appearance of a clear or slightly pink color.

The collagenous tissue membrane is subjected to a vacuum drying process under vacuum at a prescribed vacuum over a predetermined time at room temperature sufficient to dry without altering the structural and chemical properties of the tissue, preferably being placed in a freeze dryer which is set to run for 19 hours at 1100 mT and 25 degrees C. The collagenous tissue membrane, after drying, has a thickness between 100 microns to 1000 microns, typically averaging a thickness between 250 and 800 microns. The collagenous tissue membrane is cut into round, oval, square or rectangular shapes. After drying, the cut collagenous tissue membrane has at least one suture entry site formed integrally as a structurally enhanced peripheral wall that acts and performs like a grommet but without any additional parts. The suture entry site is formed by a heated tip that forms a toughened tissue membrane wall encircling each of the at least one sites. The suture entry site is heat formed having a reduced thickness puncture center or an opening either of which are surrounded by the toughened tissue membrane wall. The toughened tissue membrane wall is rigid, wherein the grommet-like feature is thickened relative to exterior surfaces of the adjacent collagenous tissue membrane. The cut collagenous tissue membrane can have two or more suture entry sites. The cut collagenous tissue membrane can be cut into a small size formed as a pledget for suturing through and attachment to a thin tissue.

In one embodiment, the cut collagenous tissue membrane has the at least one suture entry site positioned in a corner of the square or rectangular cut membrane. Each corner of the cut collagenous tissue membrane can be folded over to make a double thickness cut collagenous tissue membrane at the suture entry site. In another embodiment, the cut collagenous tissue membrane has two opposite edges, adjacent each edge is a plurality of suture entry sites. The number of the plurality of suture entry sites adjacent one edge is equal to the number of suture entry sites of the opposite edge. Preferably, the suture entry sites of one edge are offset relative to the suture entry sites of the opposite edge wherein the offset is arranged and positioned so the suture entry sites on one edge are interposed between the suture entry sites of the other edge when the cut collagenous tissue membrane is rolled or folded such that the two opposing edges are aligned. In this embodiment, the suture entry sites are configured to pass a suture helically wrapped to form a cylindrical cut collagenous tissue membrane for wrapping about a nerve, vein, artery or any other tubular or round tissue vessel.

Definitions

Meconium—is the earliest stool of a mammalian infant. Unlike later feces, meconium is composed of materials ingested during the time the infant spends in the uterus: intestinal epithelial cells, lanugo, mucus, amniotic fluid, bile, and water.

Pledget—compress or small flat mass usually of gauze or absorbent cotton that is laid over a wound or into a cavity to apply medication, exclude air, retain dressings, or absorb the matter discharged, as used herein, the pledget is made from the cut umbilical cord tissue.

BRIEF DESCRIPTION OF THE DRAWINGS

The invention will be described by way of example and with reference to the accompanying drawings in which:

FIG. 3 is a photograph of the longitudinal dissection of the umbilical cord tissue.

FIG. 4 is a photograph showing the umbilical cord after cleaning and soaking in normal saline.

FIG. 12 is an embodiment of the transplant product derived from umbilical cord having folded over corners with suture entry sites.

FIG. 13 is an embodiment of the transplant product having suture entry sites in a single layer.

FIG. 14 is another embodiment having a plurality of suture entry sites adjacent along each side.

DETAILED DESCRIPTION OF THE INVENTION

The present invention encompasses both the manufacturing of various embodiments of final transplant products 10 and the transplant products derived from human umbilical cords (UC) 2. The final umbilical cord product 10 is categorized as a thick layer of a collagenous membrane 20 freeze dried umbilical cord 2. The transplant product 10 is a semi-transparent collagenous membrane. All donated umbilical cords, preferably, are derived from cesarean section delivered placentas recovered from young, healthy consenting mothers according to established procedures from a recovering facility. Application of final processed transplant products is for homologous use as a soft tissue barrier or wound covering or for other internal wound healing applications. The tissue is for single patient use and is to only be handled by a licensed physician.

Figure 1:
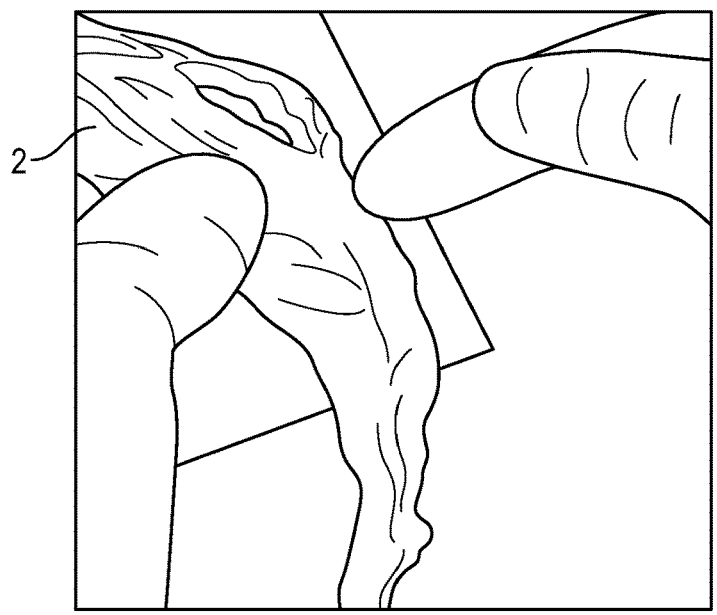
FIG. 1 is a photograph of a technician holding a cut lengthwise umbilical cord exposing the veins, arteries and Wharton's jelly.
Figure 2:
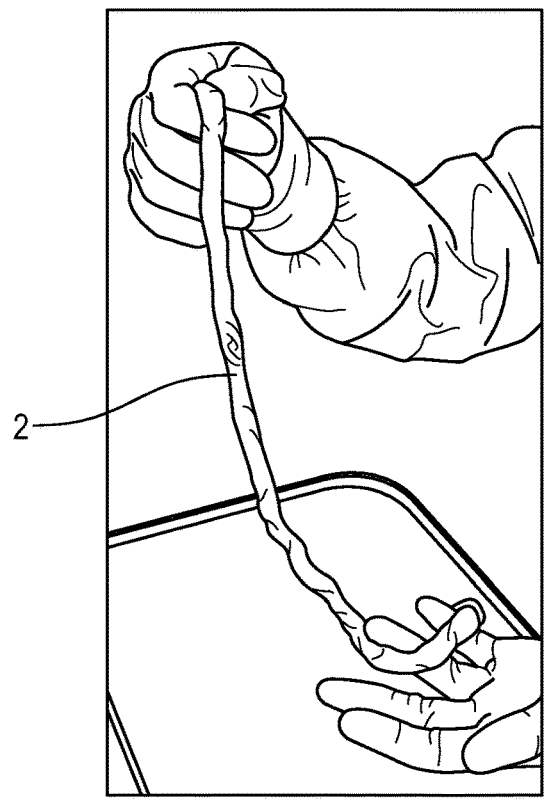
FIG. 2 is a photograph of a technician holding a length of umbilical cord during recovery.
Figure 5:
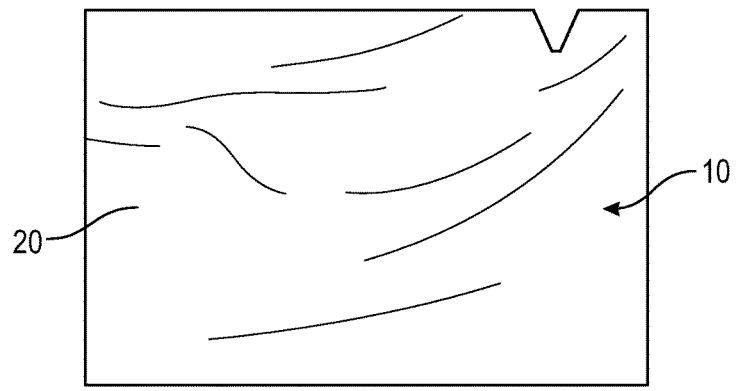
FIG. 5 is an example of the transplant product after cutting.
Figure 6:
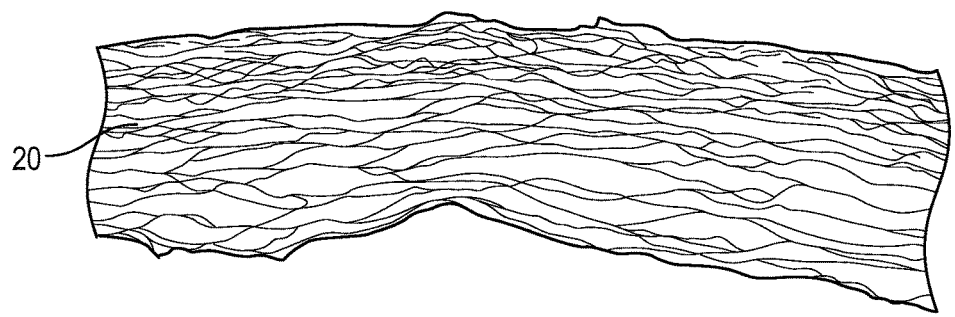
FIG. 6 is a microscoped photograph at × magnification showing the epithelial layer no longer intact.
Figure 7:
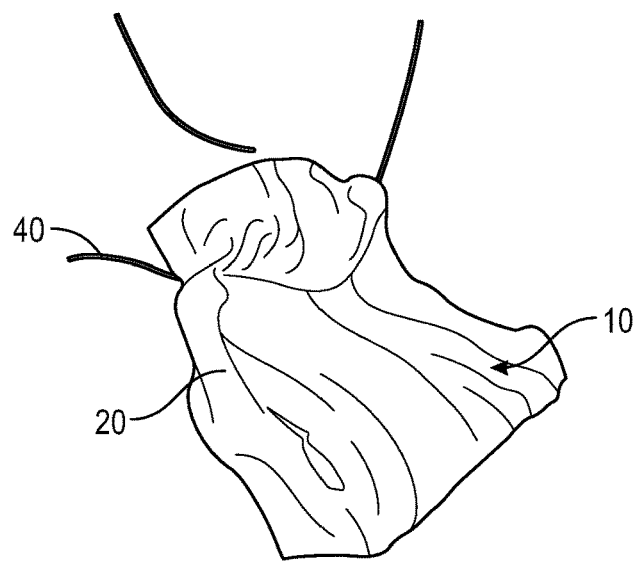
FIG. 7 is a photograph of the transplant product showing a suture passing through a folded over end.

Processing of the transplant products, as shown in the photographs of FIGS. 1-7, was conducted at approved biomedical facilities. During the processing of the final transplant product, the structural, chemical, and biochemical components of the tissue remained intact. The only solution the umbilical cord was exposed to during processing was a physiological grade normal saline solution (0.9% Sodium Chloride). This solution was used to aid in the cleaning of the tissue to remove all traces of blood and extraneous umbilical membrane tissue. The umbilical cord segments then underwent a gentle vacuum cycle to obtain a final product that was dried. The dried tissue 20 makes the final transplant product 10 by cutting and packaging in final packaging that is to be delivered to the end user. The final product can be to be stored at room temperature. The current shelf life of the final processed transplant product is expected to be 5 years based on the validation of the final packaging material used for storage.

As with all manufacturing processes, cleaning and further processing of the umbilical cord is performed using aseptic technique. Pre-cleaning microbiology cultures are taken of the umbilical cord prior to initiating the cleaning process. Once the cultures are taken, the umbilical cord is cut lengthwise and flattened exposing the inner lining. Removal of the vein, arteries and Wharton's Jelly are accomplished manually with the aid of forceps and/or razors. The umbilical cord is then exposed to a normal saline solution (0.9% Sodium Chloride) and soaked for 4-8 hours with slight agitation during this period. Acceptable cleaned umbilical cord segments of the collagenous tissue membrane 20 must be transparent in color, free of meconium, not fragile, and exhibit normal tissue integrity.

The cleaning process of the umbilical cord is performed inside an ISO Class 5, Class II biological safety cabinet (BSC) that is located inside an ISO Class 5 suite in a cleanroom. The process of cleaning the umbilical cord is performed as such to leave the structural and chemical properties of the membrane 20 intact.

Once the umbilical cord segments of the collagenous tissue membrane 20 are cleaned and meet the aforementioned acceptable criteria, they are then prepared to undergo the vacuum drying process. The cleaned umbilical cord membranes 20 are placed on a sterile plastic tray with the inner lining of the umbilical cord facing upwards and the epithelial side facing downward. A layer of medical grade foam is then gently placed on top surface or side 22 of the tissue membrane 20 and lightly pressed to ensure the membrane 20 has completely adhered to the foam. The foam is gently lifted off the plastic tray and turned over exposing the epithelial side 21 of the umbilical cord. Another layer of medical grade foam is placed over the umbilical cord membrane 20 sandwiching the tissue membrane 20 in place. The sandwiched tissues are placed into sterile drying trays with the epithelial layer side 21 facing upwards. The drying trays are then placed inside of a freeze dryer which is set to run for 19 hours at 1100 mT and 25° C. This cycle has shown to sufficiently dry the tissue without affecting the structural and chemical properties of the tissue.

The cutting of the tissue membrane 20 is performed once the vacuum drying process is complete. The dried tissue membrane 20 is removed from the freeze dryer and subsequently carefully removed from the medical grade foams. The dried umbilical cord segments are then placed on a sterile plastic cutting board. The collagenous tissue membrane 20, after drying, has a thickness between 100 microns to 1000 microns, typically averaging a thickness between 250 and 800 microns. Table 1 below exhibits the final product sizes. Once the umbilical cord segments are cut into their designated sizes using a scalpel and ruler, an orientation notch is made for the end user to denote the sidedness of the allograft. Using a sterile 5 mm skin gauge, a notch can be placed in the upper left hand corner of the membrane denoting that the epithelial side is facing upward.

Final umbilical cord product 10 sizes are provided as an exemplary list: 1 cm×1 cm, 1 cm×2 cm, 2 cm×2 cm, 2 cm×3 cm, 3 cm×3 cm, 3 cm×4 cm, 3 cm×6 cm, 3 cm×8 cm.

Figure 8:
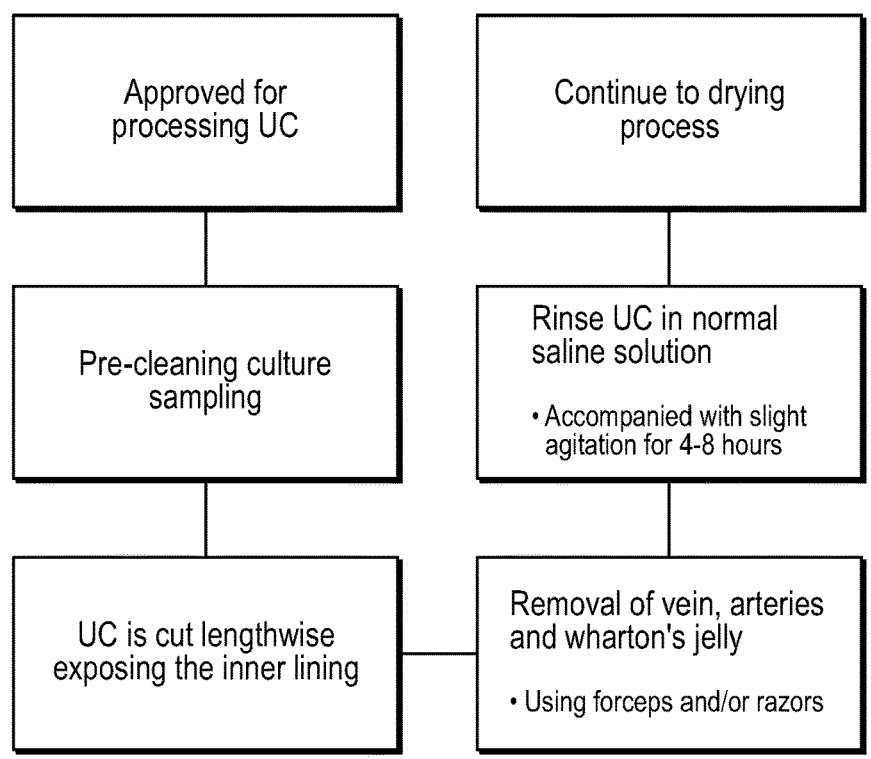
FIG. 8 is a schematic diagram of the cleaning steps.
Figure 9:
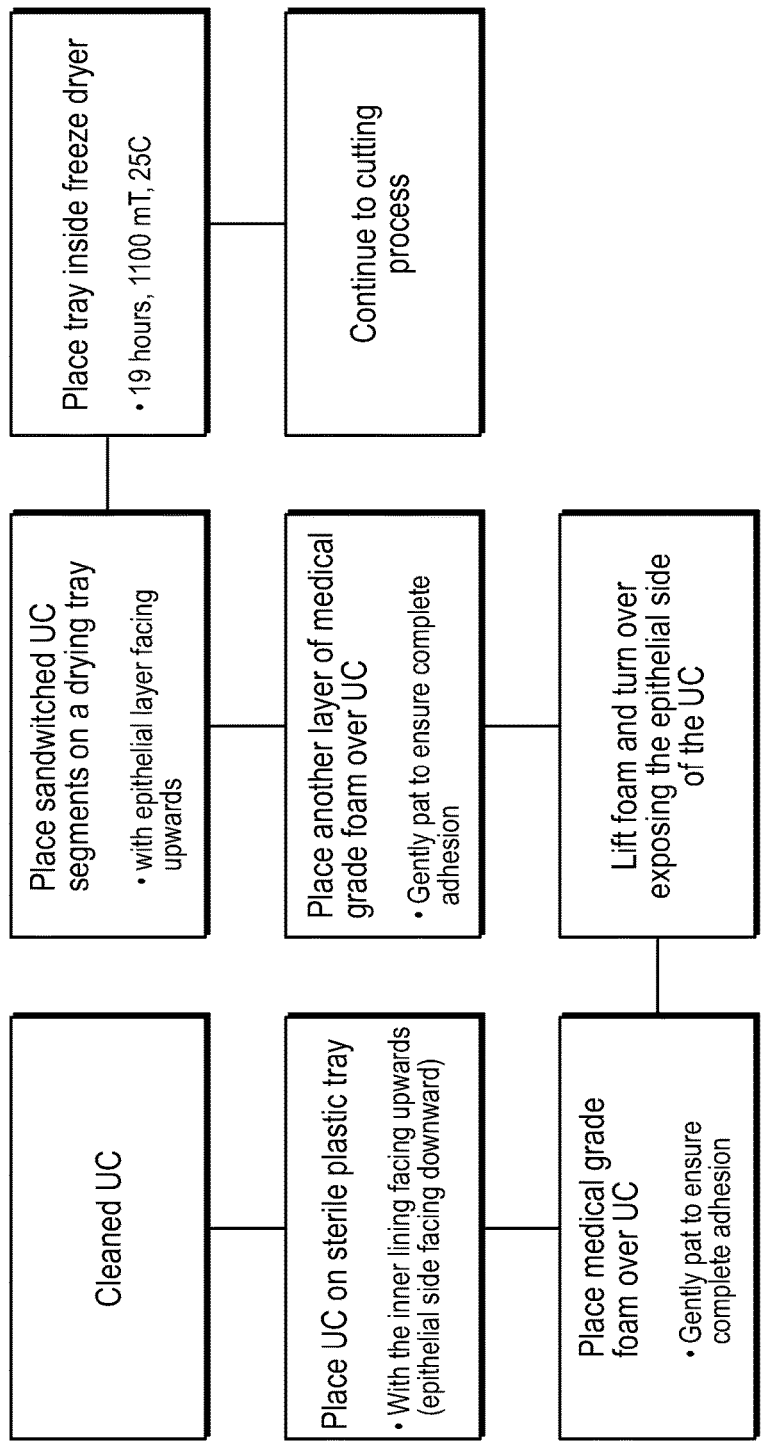
FIG. 9 is a schematic diagram of the drying steps.
Figure 10:
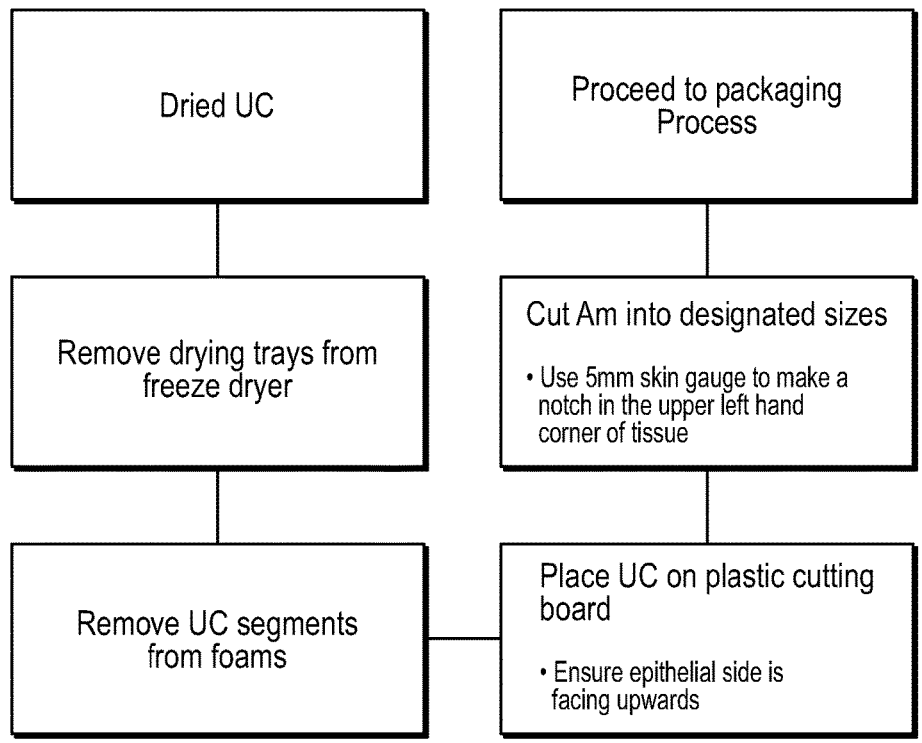
FIG. 10 is a schematic diagram of the cutting steps.
Figure 11:
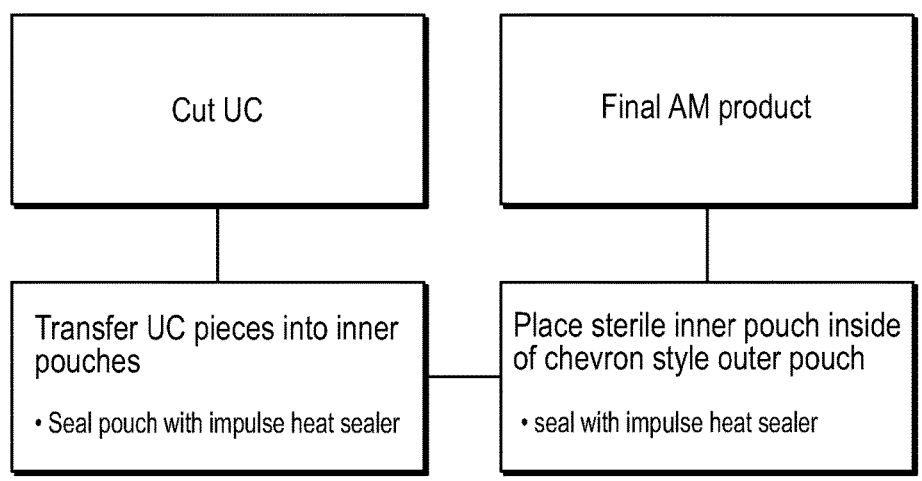
FIG. 11 is a schematic diagram of the packaging steps.
Figure 15:
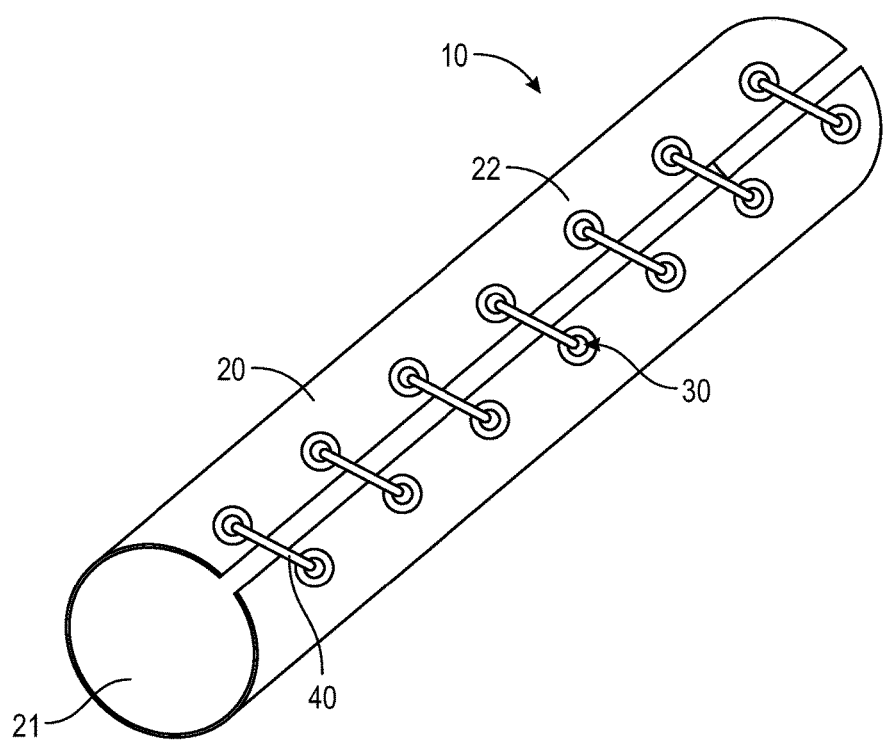
FIG. 15 is the embodiment shown in FIG. 14 rolled into a cylinder or tubular shape with a suture woven through the circumferentially offset suture entry sites.

Final processed umbilical cord membrane 20 tissues when cut form the transplant product 10 which are packaged in validated final packaging. The membrane 20 is aseptically double pouched; each pouch sealed using an impulse heat sealer. The outer packaging used is a chevron type pouch allowing the end user to easily present the sterile inner pouch containing the product to a sterile field. The packaged final product 10 is stored at room temperature until it is distributed to the end user. FIGS. 8-11 show with schematic diagrams the previously described steps of cleaning, drying, cutting and packaging respectively.

In one embodiment, the collagenous tissue membrane 20 is subjected to a vacuum drying process under vacuum at a prescribed vacuum over a predetermined time at room temperature sufficient to dry without altering the structural and chemical properties of the tissue, preferably being placed in a freeze dryer which is set to run for 19 hours at 1100 mT and 25 degrees C. Due to the thickness of the collagenous tissue membrane 20, which is typically much thicker than the thickness of tissue membranes derived from a placenta, make the umbilical cord derived membrane ideal for suturing. The collagenous tissue membrane 20 is cut into round, oval, square or rectangular shapes. After drying, the cut collagenous tissue membrane 20 can be made structurally enhanced for suturing by having at least one suture entry site 30 formed integrally as a structurally enhanced peripheral wall 32 that acts and performs like a grommet but without any additional parts. The suture entry site 30 is formed by a heated tip that forms a toughened tissue membrane wall 32 encircling each of the at least one sites 30. The suture entry site 30 is heat formed having a reduced thickness puncture center or an opening 31 either of which are surrounded by the toughened tissue membrane wall 32. The toughened tissue membrane wall 32 is rigid or generally tear resistant, wherein the grommet-like feature is thickened relative to exterior surfaces of the adjacent collagenous tissue membrane 20. The cut collagenous tissue membrane 20 can have two or more suture entry sites 30. The cut product 10 of collagenous tissue membrane 20 can be cut into a small size formed as a pledget for suturing through and attachment to a thin tissue.

In one embodiment illustrated in FIG. 13, the cut collagenous tissue membrane 20 has the at least one suture entry site 30 positioned in a corner 12 of the square or rectangular cut membrane 20. Each corner 12 of the cut collagenous tissue membrane 20 can be folded over to make a double thickness cut collagenous tissue membrane 20 at the suture entry site 30 wherein the top surface or side 22 is covered at the corners 12 by the epithelial side 21, as shown in FIG. 12. In another embodiment, the cut collagenous tissue membrane 20 has two opposite edges 26, 27, adjacent each edge 26, 27 is a plurality of suture entry sites. The number of the plurality of suture entry sites adjacent one edge 26 either one less, equal to or one more than the number of suture entry sites 30 of the opposite edge 27, as shown 8 and 9 suture entry sites 30 on the respective edges 26, 27 in FIG. 14. Preferably, the suture entry sites 30 of one edge 27 are offset relative to the suture entry sites 30 of the opposite edge 26 wherein the offset is arranged and positioned so the suture entry sites on one edge are interposed between the suture entry sites 30 of the other edge when the cut collagenous tissue membrane 20 is rolled or folded such that the two opposing edges 26, 27 are aligned. In this embodiment, the suture entry sites 30 are configured to pass a suture 40 helically wrapped to form a cylindrical cut collagenous tissue membrane 20 for wrapping about a nerve, vein, artery or any other tubular or round tissue vessel.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. A transplant product derived from human umbilical cord comprising:
   a collagenous tissue membrane of umbilical cord, configured as a layer of a soft tissue barrier or wound covering or other internal or external wound healing attachment; and wherein structural, chemical and biochemical properties of the collagenous tissue membrane are retained after the collagenous tissue membrane is cleaned removing veins, arteries and Wharton's jelly without exposing the collagenous tissue membrane to chemical and biochemical property altering chemicals and wherein the collagenous tissue membrane is dried and then cut into square or rectangular shapes, after drying the dried cut collagenous tissue membrane has a plurality of suture entry sites, each suture entry site formed integrally as a structurally enhanced peripheral wall that acts and performs like a grommet but without any additional parts, and wherein each of the suture entry sites is formed by a heated tip that forms a toughened tissue membrane wall encircling each of the suture entry sites wherein each of the suture entry sites is heat formed having a reduced thickness puncture center surrounded by the toughened tissue membrane wall, the toughened tissue membrane wall being rigid and thickened relative to exterior surfaces of the collagenous tissue membrane surrounding the grommet, the exterior surfaces having a thickness between 100 to 1000 microns;
   wherein the cut collagenous tissue membrane has two opposite edges, adjacent each edge is at least one of the plurality of suture entry sites;
   wherein a number of the plurality of the suture entry sites adjacent one edge is one less, equal to or one more than a number of the plurality of the suture entry sites of the opposite edge;
   wherein the plurality of the suture entry sites of one edge are offset relative to the plurality of the suture entry sites of the opposite edge wherein the offset is arranged and positioned so the suture entry sites on one edge are interposed between the suture entry sites of the other edge when the cut collagenous tissue membrane is rolled or folded such that the two opposing edges are aligned;
   wherein the plurality of the suture entry sites of each edge are configured to pass a suture through the layer of the square or rectangular shape which is rolled or folded held by the suture so the two opposing edges are aligned to form a cylindrical cut collagenous tissue membrane for wrapping about a nerve, vein, artery or any other tubular or round tissue vessel; and
   wherein the transplant product has the collagenous tissue membrane dried, the dried membrane having the thickness in the range of 100 to 1000 microns.

2. The transplant product of claim 1 wherein the collagenous tissue membrane is soaked in normal saline solution under mild agitation for a predetermined time to structurally increase tear resistance of the collagenous tissue membrane.

3. The transplant product of claim 2 wherein the collagenous tissue membrane is free of meconium.

4. The transplant product of claim 3 wherein the collagenous tissue membrane has a transparent or translucent appearance of a clear or pink color.

5. The transplant product of claim 1 wherein the collagenous tissue membrane is subjected to a vacuum drying process under vacuum at a prescribed vacuum over a predetermined time at room temperature sufficient to dry without altering the structural and chemical properties of the collagenous tissue membrane.

* * * * *